(12) United States Patent
Jain et al.

(10) Patent No.: US 9,566,299 B2
(45) Date of Patent: Feb. 14, 2017

(54) ORAL PHARMACEUTICAL COMPOSITION OF ALIPHATIC AMINE POLYMER OR SALTS THEREOF

(71) Applicant: WOCKHARDT LIMITED, Aurangabad (IN)

(72) Inventors: Girish Kumar Jain, Delhi (IN); Venkataramana Naidu, Secunderabad (IN); Abdul Rehman Khan, Aurangabad (IN); Amar Agarwal, Aurangabad (IN); Srikanth Pattipati, Andhra Pradesh Nizamabad (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 0 days.

(21) Appl. No.: 14/766,327

(22) PCT Filed: Feb. 5, 2014

(86) PCT No.: PCT/IB2014/058797
§ 371 (c)(1),
(2) Date: Aug. 6, 2015

(87) PCT Pub. No.: WO2014/122586
PCT Pub. Date: Aug. 14, 2014

(65) Prior Publication Data
US 2015/0374744 A1    Dec. 31, 2015

(30) Foreign Application Priority Data

Feb. 8, 2013   (IN) .......................... 383/MUM/2013
Feb. 14, 2013  (IN) .......................... 445/MUM/2013

(51) Int. Cl.
*A61K 9/28* (2006.01)
*A61K 31/785* (2006.01)

(52) U.S. Cl.
CPC ............. *A61K 31/785* (2013.01); *A61K 9/282* (2013.01); *A61K 9/2866* (2013.01); *A61K 9/2893* (2013.01)

(58) Field of Classification Search
CPC .. A61K 9/2866; A61K 31/785; A61K 9/2018; A61K 9/2027; A61K 31/765
See application file for complete search history.

(56) References Cited

U.S. PATENT DOCUMENTS

2010/0008988 A1*  1/2010  Mehta ................... A61K 31/765
                                                                424/474
2011/0159087 A1*  6/2011  Sathe ................... A61K 9/2018
                                                                424/452

* cited by examiner

*Primary Examiner* — Audrea Buckley
(74) *Attorney, Agent, or Firm* — Bio Intellectual Property Services LLC (Bio IPS); O. (Sam) Zaghmout

(57) ABSTRACT

The present invention relates to an oral pharmaceutical composition of aliphatic amine polymer or salts thereof comprising mixture of water and organic solvent(s) and/or less than of about 10% of plasticizing agent in the coating composition. In particular, present invention relates to a coated pharmaceutical composition of aliphatic amine polymer or salt thereof which comprises mixture of water and organic solvent(s) and less than of about 10% of plasticizing agent in coating. The invention also includes process of preparing such composition.

3 Claims, No Drawings

ORAL PHARMACEUTICAL COMPOSITION OF ALIPHATIC AMINE POLYMER OR SALTS THEREOF

FIELD OF THE INVENTION

The present invention relates to an oral pharmaceutical composition of aliphatic amine polymer or salts thereof comprising less than of about 10% of plasticizing agent in the coating composition and/or mixture of water and organic solvent(s) as coating solvent. By using a mixture of water and organic solvent(s) and/or less than of about 10% of plasticizer in the coating, a robust coat which can control the swelling of the composition can be prepared.

BACKGROUND OF THE INVENTION

The aliphatic amine polymer is a cross-linked polyallylamine with a pharmaceutically acceptable acid. The aliphatic amine polymer is an epichlorohydrin-cross-linked polyallylamine with a pharmaceutically acceptable acid, such as sevelamer, sevelamer hydrochloride, colesevelam or its hydrochloride salt.

The colesevelam hydrochloride is a non-absorbable, polymeric and a high-capacity bile acid-binding molecule. It is also a lipid-lowering and glucose-lowering agent intended for oral administration. Colesevelam hydrochloride is poly (allylamine hydrochloride) cross-linked with epichlorohydrin and alkylated with 1-bromodecane and (6-bromohexyl)-trimethylammonium bromide. Colesevelam hydrochloride is hydrophilic and insoluble in water. Chemically, allylamine polymer with 1-chloro-2,3-epoxypropane, [6-(allylamino)-hexyl]trimethylammonium chloride and N-allyldecylamine, hydrochloride and is represented by the following formula:

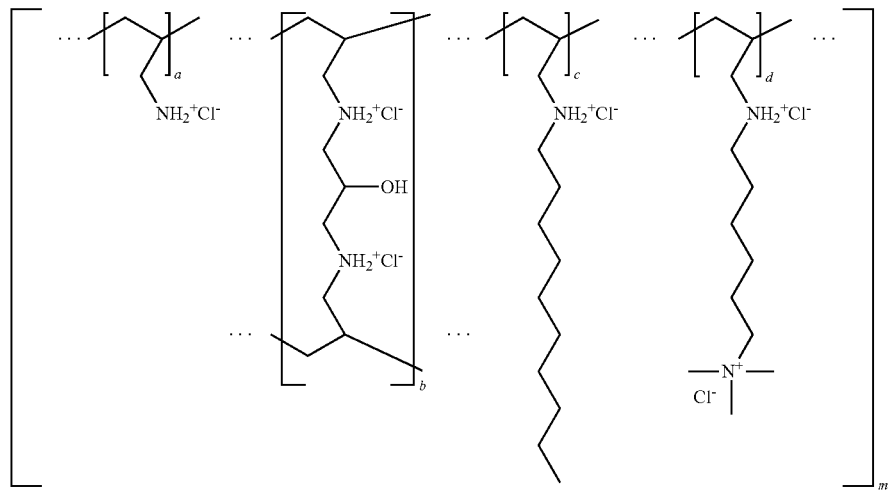

In the structure, m represents a number ≥100 to indicate an extended polymer network.

Colesevelam hydrochloride is approved in United States under the proprietary name Welchol® as oral tablet and marketed by Daiichi Sankyo.

Welchol® is indicated as an adjunct to diet and exercise to reduce elevated low-density lipoprotein cholesterol (LDL-C) in adults with primary hyperlipidemia (Fredrickson Type IIa) as monotherapy or in combination with HMG CoA) reductase inhibitor (statin) and as an adjunct to diet and exercise to improve glycemic control in adults with type 2 diabetes mellitus.

U.S. Pat. No. 7,229,613 discloses a method for treating hyperglycemia and/or reducing serum glucose levels in a patient that includes administering to the patient a therapeutically effective amount of colesevelam or salts thereof.

U.S. Pat. No. 6,733,780 discloses a compressed tablet comprising a hydrophilic core comprising at least or about 95 weight % of poly (allylamine) or a salt thereof and a water-based coating comprising cellulose derivative and plasticizing agent. The patent discloses coating composition comprising hydroxypropylmethylcellulose and a plasticizer. The disclosed coating composition contains at least 23% of diacetylated monoglyceride as a plasticizing agent.

The U.S. Patent Application No. 2010/0008988 discloses pharmaceutical compositions comprising less than about 95% by weight of aliphatic amine polymers of sevelamer hydrochloride, sevelamer carbonate and colesevelam hydrochloride, and methods of preparing pharmaceutical compositions thereof.

The U.S. Patent Application No. 2010/0330175 discloses a pharmaceutical composition comprising dry cross-linked polyallylamine and water soluble excipient comprising polyols and polyethylene glycol.

The U.S. Patent Application No. 2011/0159087 discloses a pharmaceutical composition comprising wet granulated bile acid sequestrants composition, wherein the composition is free of reducing sugar.

The colesevelam hydrochloride tends to be very hygroscopic and thus will swell immediately upon contact with the inside of the mouth. Thus it was believed that coating such tablets with aqueous based coating would be difficult because the hygroscopic tablets would swell during the coating process.

The prior arts disclosure suggests that use of a relatively high amount of diacetylated monoglyceride as plasticizing agent in coating composition to overcome the tablet-swelling problem and to stabilize the pharmaceutical compositions of poly allylamines or a salt thereof.

Thus, there still exists an enduring need to develop an improved and stable pharmaceutical composition of aliphatic amine polymers which will provides an alternative to existing formulation of colesevelam hydrochloride.

SUMMARY OF THE INVENTION

In one aspect, there is provided an oral pharmaceutical composition comprising a core, which comprises of an aliphatic amine polymer or salt thereof and optionally with one or more pharmaceutically acceptable excipients, and at least one layer coated over said core, which comprises mixture of water and organic solvent(s) in the ratio of about 90:10 to about 10:90 and/or less than about of 10% w/w of one or more plasticizing agents and optionally one or more pharmaceutically acceptable excipients.

In another aspect, there is provided an oral pharmaceutical composition comprising a core, which comprises of colesevelam or salt thereof and optionally with one or more pharmaceutically acceptable excipients, and at least one layer coated over said core, which comprises of less than about of 10% w/w of one or more plasticizing agents, and optionally one or more pharmaceutically acceptable excipients.

In another aspect, the amount of plasticizer in the coating composition is less than about 8% w/w, preferably less than about 5% w/w.

In another aspect, there is provided an oral pharmaceutical composition comprising a core, which comprises of an aliphatic amine polymer or salt thereof and optionally with one or more pharmaceutically acceptable excipients, and at least one layer coated over said core, which comprises of less than about of 10% w/w of diacetylated monoglyceride, and optionally one or more pharmaceutically acceptable excipients.

In another aspect, there is provided a process for the preparation of an oral pharmaceutical composition of an aliphatic amine polymer or salt thereof, which process comprises steps of:
(a) mixing the aliphatic amine polymer or salt thereof with one or more pharmaceutically acceptable excipients; compressing the mixture to form a core; and
(b) coating the said core with a composition which comprises of mixture of water and organic solvent(s) in the ratio of about 90:10 to about 10:90 and/or less than 10% w/w of one or more plasticizing agents, and optionally one or more pharmaceutically acceptable excipients.

In another aspect, there is provided a process for the preparation of an oral pharmaceutical composition of an aliphatic amine polymer or salt thereof, which process comprises steps of:
(a) preparing a core which comprises of an aliphatic amine polymer or salt thereof, and optionally one or more pharmaceutically acceptable excipients; and
(b) coating the said core with a composition which comprises of less than about 10% w/w of one or more plasticizing agents, water, one or more organic solvent, and optionally one or more pharmaceutically acceptable excipients.

In another aspect, there is provided an oral pharmaceutical composition comprising a core, which comprises of an aliphatic amine polymer or salt thereof and optionally with one or more pharmaceutically acceptable excipients, and at least one layer coated over said core, which comprises of less than about of 10% w/w of plasticizing agent, polymer and optionally one or more pharmaceutically acceptable excipients.

In another aspect, there is provided an oral pharmaceutical composition comprising a core, which comprises of an aliphatic amine polymer or salt thereof and optionally with one or more pharmaceutically acceptable excipients, and at least one layer coated over said core, which comprises plasticizing agent and aliphatic amine polymer in the ratio of about 1:4 to about 1:45, preferably 1:43 w/w of the total weight of the coating composition.

In another aspect, there is provided an oral pharmaceutical composition used for the Primary Hyperlipidemia and Type 2 Diabetes Mellitus as an adjunct to diet and exercise.

DETAILED DESCRIPTION OF THE INVENTION

The inventors of the present invention have surprisingly found that by using the mixture of water and organic solvent(s) in the range of about 90:10 to about 10:90 and/or less than about of 10% w/w of plasticizing agent in coating composition, the tablet-swelling problem can be avoided significantly and also provides ease to coating operation.

The inventors of the present invention empirically found that using mixture of water and organic solvent(s) and/or a judicial amount of plasticizing agent in the coating compositions has a direct effect on the tablet swelling and practical operations. In particular, the inventors have found that judicially using mixture of water and organic solvent(s) in coating solution or dispersion in the range of about 10:90 to about 90:10 and less than about of 10% w/w of plasticizing agent, for example, diacetylated monoglyceride can effectively curb the tablet swelling and provides ease to coating operation of aliphatic amine polymers (e.g. colesevelam hydrochloride) and eventually may control generation of impurities. As a result, inventors of the present invention have found a novel way of preparing the pharmaceutical composition of aliphatic amine polymers which can significantly control tablet swelling and meets the desired parameters.

The present invention relates to a novel coated pharmaceutical composition of aliphatic amine polymer or salt thereof which coating comprises mixture of water and organic solvent(s) and/or less than about 10% of plasticizing agent.

The term "aliphatic amine polymer" used throughout the specification refers to not only aliphatic amine polymer per se, but also its free base, other pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof.

Aliphatic amine polymer suitable for use in the composition of the present invention may include, but not limited to bile acid sequestrants such as colesevelam and sevelamer.

The compositions of the present invention are oral compositions of colesevelam hydrochloride that improve shelf-life and provide palliative pharmaceutical composition of colesevelam hydrochloride.

In an another embodiment, the pharmaceutical composition of aliphatic amine polymer comprises a core comprising aliphatic amine polymer and one or more pharmaceutically acceptable excipients and at least one layer coated over said core comprises water, one or more organic solvents, one or more plasticizing agents, and optionally one or more pharmaceutically acceptable excipients; wherein the composition is stable when stored for real time study condition at 25° C. and 60% relative humidity or for accelerated study condition at 40° C. and 75% relative humidity for at least 3 months.

In an embodiment, the pharmaceutical composition of the present invention comprising colesevelam hydrochloride and coating comprising less than 10% w/w of plasticizing agent and optionally with one or more pharmaceutically acceptable excipients, wherein the composition is stable when stored at 25° C. and 60% relative humidity or at 40° C. and 75% relative humidity for at least 3 months.

In another embodiment, the pharmaceutical composition of the present invention comprises aliphatic amine polymer in an amount of less than of about 80% of the core weight.

In a further embodiment, the composition substantially free of impurities like unknown or degradation products when stored at 25° C. and 60% relative humidity or at 40° C. and 75% relative humidity for 3 months.

The pharmaceutical composition of the present invention may be developed in the form of a dosage form suitable of oral administration.

Dosage forms include solid dosage forms but not limited to tablets, powders, capsules, suppositories, sachets, troches and lozenges, as well as liquid syrups, suspensions and elixirs. The tablet can be coated or uncoated tablet.

The term "pharmaceutically acceptable excipient" includes a pharmaceutically acceptable material, composition or vehicle, suitable for administering an active pharmaceutical ingredient. Each excipient should be "acceptable" in the sense of being compatible with the other ingredients of the formulation and not injurious to the patient. Excipients include diluents, binders, disintegrants, glidants, lubricants, flavoring, and others.

Diluents increase the bulk of a solid pharmaceutical composition. Exemplary diluents for solid compositions include, but are not limited to, microcrystalline cellulose, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates, potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Exemplary binders for solid pharmaceutical compositions include, but are not limited to, acacia, alginic acid, carbomer, carboxymethylcellulose sodium, dextrin, ethyl cellulose, gelatin, guar gum, hydrogenated vegetable oil, hydroxyethyl cellulose, hydroxypropyl cellulose, hydroxypropyl methyl cellulose, liquid glucose, magnesium aluminum silicate, maltodextrin, methylcellulose, polymethacrylates, povidone, pregelatinized starch, sodium alginate and starch.

Disintegrants increase the dissolution rate of a compacted solid pharmaceutical composition in the patient's stomach, for example. Exemplary disintegrants include, but are not limited to, alginic acid, carboxymethylcellulose calcium, carboxymethylcellulose sodium, colloidal silicon dioxide, croscarmellose sodium, crospovidone, guar gum, magnesium aluminum silicate, methyl cellulose, microcrystalline cellulose, polacrilin potassium, powdered cellulose, pregelatinized starch, sodium alginate, sodium starch glycolate and starch.

Glidants can be added to improve the flowability of a non-compacted solid composition and to improve the accuracy of dosing. Exemplary excipients that may function as glidants include colloidal silicon dioxide, magnesium trisilicate, powdered cellulose, starch, talc and tribasic calcium phosphate.

A lubricant can be added to the composition to reduce adhesion and ease the release of the product from the dye. Exemplary lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Tablets may be coated in a rotary pan coater as is known in the art or any other conventional coating apparatus such as a column coater or a continuous coater.

The coating composition comprises polymer and plasticizing agent. The polymer can be selected from but not limited cellulosic ethers such as hydroxypropylmethylcellulose (HPMC) and hydroxypropyl cellulose. The plasticizing agent selected from group comprising acetylated monoglyceride, triacetin, polyethylene glycol, triethyl citrate, a polysorbate, preferably diacetylated monoglyceride either alone or in combination thereof. The coating composition can further include a pigment to provide a tablet coating of the desired color. For example, to produce a white coating, a white pigment can be selected such as titanium dioxide.

In an embodiment, the ratio of amount of plasticizing agent and polymer in the coating composition according to the present invention is in the range of about 1:4 to about 1:45, preferably 1:43 w/w.

In an embodiment, the ratio of amount of water and organic solvent(s) in the coating composition according to the present invention is in the range of about 90:10 to about 10:90, preferably 70:30 to 30:70, more preferably 40:10 to 10:40 v/v.

The present invention is further illustrated by the following examples which are provided merely to be exemplary of the invention and do not limit the scope of the invention. Certain modifications and equivalents will be apparent to those skilled in the art and are intended to be included within the scope of the present invention.

Example 1

Colesevelam Hydrochloride Tablet

TABLE 1

| Sr. No. | Ingredients | Quantity in Mg/Tablet | % W/W |
|---|---|---|---|
| Intragranular Ingredients | | | |
| 1. | Colesevelam Hydrochloride | 625.0 | 74.40 |
| 2. | Microcrystalline Cellulose (Avicel PH 102) | 50.0 | 5.96 |
| 3. | Colloidal silicon dioxide (Aerosil 200) | 4.5 | 0.54 |
| 4. | Magnesium stearate | 1.0 | 0.12 |
| Extra granular ingredients | | | |
| 5. | Microcrystalline Cellulose (Avicel PH 102) | 153.0 | 18.21 |
| 6. | Colloidal silicon dioxide (Aerosil 200) | 4.5 | 0.54 |
| 7. | Magnesium stearate (Hyqual) | 2.0 | 0.24 |
| | Tablet core weight | 840.0 | 100 |

Process for Preparing Uncoated Core:

The weighed amount of colesevelam Hydrochloride was co sifted with colloidal silicon dioxide and Microcrystalline Cellulose (MCC) through 30# mesh. To this magnesium stearate passed through #60 mesh was added and blended for 5 minutes in double cone blender. The obtained blend was compacted using roll compactor using suitable compaction parameters. The obtained flakes were milled using oscillating granulator through #25 mesh so that all granules of below 25#. The #25 mesh passed granules were further sifted through 60# mesh and fraction above #60 collected separately. Compaction process was repeated for below 60# fraction till 50 to 60% of above 60# granules are obtained. These obtained granules were blended in double cone blender for 5 minutes with MCC and Colloidal silicon dioxide, previously passed through #40 mesh. These obtained granules were lubricated with pre sifted (through 60 mesh) magnesium stearate, in Double Cone Blender for 3 minutes and then compressed into tablet using suitable punches.

The Colesevelam Hydrochloride tablet obtained from example 1 was coated with various coating composition comprising hydroxypropylmethylcellulose and diacetylated monoglycerides present in different proportion. The various illustrative examples are as follows:

Example 2

Coating Composition

TABLE 2

| Sr. No. | Ingredients | Quantity in Mg/Tablet | % W/W |
|---|---|---|---|
| 1. | Hydroxypropylmethylcellulose (HPMC) 15 Cp | 49.28 | 48.89 |
| 2. | Hydroxypropylmethylcellulose (HPMC) 5 Cp | 49.28 | 48.89 |
| 3. | Di-Acetylated Monoglycerides | 2.25 | 2.23 |
| 4. | Isopropyl Alcohol*** | 154.56 | — |
| 5. | Purified Water*** | 618.24 | — |
| | Total weight | 100.8 | |

***Removed during processing of drying.

Example 3

Tablet Coating with Hydro-Alcoholic Dispersion

TABLE 3

| S. No | Coating composition | Ingredients/ Composition | Ratio of IPA: water | % w/w | % Weight gain/ Tab | Mg/ Tab | Disintegration time* |
|---|---|---|---|---|---|---|---|
| 1. | Coating Composition I | HPMC 15 cps | 20:80 | 48.89 | 8 | 32.85 | 7 min |
| | | HPMC 5 cps | | 48.89 | | 32.85 | |
| | | DAMG | | 2.23 | | 1.49 | |
| 2. | | HPMC 15 cps | 20:80 | 48.89 | 10 | 48.50 | 10 min |
| | | HPMC 5 cps | | 48.89 | | 48.50 | 30 sec |
| | | DAMG | | 2.23 | | 2.21 | |
| 3. | | HPMC 15 cps | 20:80 | 48.89 | 12 | 61.59 | 16 min |
| | | HPMC 5 cps | | 48.89 | | 61.59 | |
| | | DAMG | | 2.23 | | 2.81 | |
| 4. | | HPMC 15 cps | 40:60 | 48.89 | 8 | 32.85 | 7-8 min |
| | | HPMC 5 cps | | 48.89 | | 32.85 | |
| | | DAMG | | 2.23 | | 1.49 | |
| 5. | | HPMC 15 cps | 10:90 | 48.89 | 13 | 53.38 | 11 min |
| | | HPMC 5 cps | | 48.89 | | 53.38 | 38 sec |
| | | DAMG | | 2.23 | | 2.44 | |
| 6. | | HPMC 15 cps | 20:80 | 61.59 | 15 | 48.88 | 16 min |
| | | HPMC 5 cps | | 61.59 | | 48.88 | |
| | | DAMG | | 2.81 | | 2.23 | |

*Checked on 6 tablets in purified water

Process for Coating with Hydro-Alcoholic Dispersion:

The weighed amount of Hydroxypropylmethylcellulose and Di-Acetylated Monoglycerides were dissolved or dispersed in hydro-alcoholic solvent. The obtained coating solution or dispersion was applied to compressed cores until a weight gain of approximately about 7 to about 15 percent was achieved. The coating composition was prepared by using water:alcohol in the ratio of about 90:10 to about 10:90. The hydro-alcoholic solvent used in coating solution was completely removed during drying process.

Example 4

Tablet Coating with Aqueous Dispersion

TABLE 4

| S. No. | Coating composition | Ingredients/ Composition | % w/w | % Weight gain/ Tab | Mg/ Tab. | Disintegration time* |
|---|---|---|---|---|---|---|
| 1. | Coating composition I | HPMC 15 cps | 48.885 | 8 | 32.85 | 4 min |
| | | HPMC 5 cps | 48.885 | | 32.85 | 36 sec |
| | | DAMG | 2.23 | | 1.49 | |
| 2. | Coating composition II | HPMC 15 cps | 70.00 | 8 | 47.05 | 5 min |
| | | HPMC 5 cps | 27.77 | | 18.66 | 20 sec |
| | | DAMG | 2.23 | | 1.49 | |
| 3. | Coating composition II | HPMC 15 cps | 70.00 | 11 | 64.68 | 6-8 min |
| | | HPMC 5 cps | 27.77 | | 25.65 | |
| | | DAMG | 2.23 | | 2.07 | |
| 4. | Coating composition III | HPMC 50 cps | 50.000 | 8 | 33.60 | 5 min |
| | | HPMC 5 cps | 47.77 | | 32.10 | 36 sec |
| | | DAMG | 2.23 | | 1.49 | |

*Checked on 6 tablets in purified water

Process for Coating Tablet with Aqueous Dispersion:

The required amount of HPMC and DAMG was dispersed in water and stirred for 40 minutes till clear solution or dispersion without lumps was obtained. The compressed core tablet obtained in Example 1 was added in coating pan. The coating was started after setting the desired parameters (RPM, temperature and atomization speed) and continued the coating till the target weight gain was achieved.

Example 5

Tablet Coating with Non-Aqueous Dispersion

TABLE 5

| Sr. No. | Coating Composition (Ingredient) | Quantity in Mg/Tablet | % W/W | % Weight gain/Tab | Disintegration time* |
|---|---|---|---|---|---|
| 1. | HPMC 15 Cp | 47.05 | 70.00 | 8 | 14 Min |
| 2. | HPMC 5 Cp | 18.66 | 27.77 | | |
| 3. | Di-Acetylated Monoglycerides | 1.49 | 2.23 | | |
| 4. | IPA + DCM** | 820.8 ml + 547.2 ml | — | | |
| | Total coating weight gain | 67.2 | | | |

**Removed during processing of drying.

Process for Coating Tablet with Aqueous Dispersion:

The required amount of HPMC and DAMG was dispersed in Isopropyl alcohol and Dichloromethane and stirred for 40 minutes till clear solution or dispersion without lumps was obtained. The compressed core tablet obtained in Example 1 was added in coating pan. The coating was started after setting the desired parameters (RPM, temperature and atomization speed) and continued the coating till the target weight gain was achieved.

The various coated tablets obtained from examples 4 illustrates that tablets do not match the disintegration time (DT) when compared with Reference product. The disintegration time (DT) for Reference product is as follows in various media:

TABLE 6

| | Disintegration time (in various media) | | |
| --- | --- | --- | --- |
| | Water | SIF | SGF |
| Reference product | 11 min | 8 min | 6 min |

The coated tablets obtained from example 5 illustrate that tablets match the disintegration time (DT) when compared with Reference product. But the various problems like logo bridging, change in film property like from transparent film to opaque film were observed.

The various coated tablets obtained from examples 3 illustrative that tablets according to present invention match the Disintegration time (DT) when compared with Reference product and various problems like logo bridging, change in film property like from transparent film to opaque film were not observed.

The invention claimed is:

1. An oral pharmaceutical composition comprising
   a) a core comprising colesevelam hydrochloride in an amount of 625 mg and
   b) a coating layer coated over said core (a) with a coating composition comprising, (i) di-acetylated monoglyceride in an amount of 2.25 mg, (ii) hydroxypropylmethylcellulose (HPMC) 15 Cp in an amount of 49.28 mg per tablet, (iii) hydroxypropylmethylcellulose (HPMC) 5 Cp in an amount of 49.28 mg per tablet, and (iv) mixture of water and isopropyl alcohol in the ratio of about 90:10 to about 10:90.

2. The oral pharmaceutical composition of claim 1, wherein the core is prepared using a roll compaction process.

3. A method for the treatment of primary hyperlipidemia and type 2 diabetes mellitus as an adjunct to diet and exercise comprising administering the pharmaceutical composition of claim 1.

* * * * *